United States Patent
Dalton et al.

(10) Patent No.: US 10,342,961 B2
(45) Date of Patent: Jul. 9, 2019

(54) IMPLANTABLE CHAMBER FOR COLLECTION AND SUPPLY OF INTERSTITIAL FLUID

(71) Applicants: Michael J. Dalton, Evanston, IL (US); Jordan M. Dalton, Libertyville, IL (US); Natan A. Pheil, Chicago, IL (US)

(72) Inventors: Michael J. Dalton, Evanston, IL (US); Jordan M. Dalton, Libertyville, IL (US); Natan A. Pheil, Chicago, IL (US)

( * ) Notice: Subject to any disclaimer, the term of this patent is extended or adjusted under 35 U.S.C. 154(b) by 707 days.

(21) Appl. No.: 14/796,927

(22) Filed: Jul. 10, 2015

(65) Prior Publication Data

US 2017/0007808 A1 Jan. 12, 2017
US 2018/0056049 A9 Mar. 1, 2018

Related U.S. Application Data

(63) Continuation-in-part of application No. 14/182,418, filed on Feb. 18, 2014.

(60) Provisional application No. 61/766,111, filed on Feb. 18, 2013, provisional application No. 62/022,795, filed on Jul. 10, 2014.

(51) Int. Cl.
  *A61M 27/00* (2006.01)
(52) U.S. Cl.
  CPC ....... *A61M 27/002* (2013.01); *A61M 2205/75* (2013.01)
(58) Field of Classification Search
  CPC ............ A61M 2205/75; A61M 27/002; A61M 27/006; A61M 27/008; A61M 5/1407; A61M 5/14276; A61M 5/1723; A61M 2202/09; A61M 2005/14208; A61F 2/022
  See application file for complete search history.

(56) References Cited

U.S. PATENT DOCUMENTS

| | | | |
|---|---|---|---|
| 3,750,194 A | 8/1973 | Summers | |
| 4,368,737 A * | 1/1983 | Ash | A61M 1/285 604/175 |
| 5,011,472 A | 4/1991 | Aebischer | |
| 5,425,764 A * | 6/1995 | Fournier | A61F 2/022 604/6.09 |
| 6,217,609 B1 * | 4/2001 | Haverkost | A61F 2/90 623/1.13 |
| 6,511,473 B2 | 1/2003 | Bartha et al. | |
| 7,043,295 B2 | 5/2006 | Starkebaum | |
| 7,637,897 B2 | 12/2009 | Ginggen | |
| 8,702,684 B2 | 4/2014 | Bodor et al. | |

(Continued)

OTHER PUBLICATIONS

STIC Search, Sep. 1, 2015, 14 pages.
(Continued)

*Primary Examiner* — Bhisma Mehta
*Assistant Examiner* — Hamza A Darb
(74) *Attorney, Agent, or Firm* — Klintworth & Rozenblat IP LLP

(57) ABSTRACT

A system for redistributing interstitial fluid within a mammal is disclosed. The system comprises an implantable accumulation chamber, a confined flow passageway such as a catheter in communication with the accumulation chamber, and a liquid transfer pump for dispensing accumulated interstitial fluid from the accumulation chamber to a predetermined body site via the confined flow passageway.

17 Claims, 10 Drawing Sheets

(56) References Cited

U.S. PATENT DOCUMENTS

| | | | |
|---|---|---|---|
| 2004/0024358 A1* | 2/2004 | Meythaler | A61M 5/14 |
| | | | 604/113 |
| 2008/0039792 A1 | 2/2008 | Meng | |
| 2009/0287178 A1* | 11/2009 | Herbert | A61M 27/002 |
| | | | 604/500 |
| 2010/0204683 A1* | 8/2010 | Bodor | A61F 2/022 |
| | | | 604/891.1 |
| 2010/0228179 A1* | 9/2010 | Thomas | A61M 27/006 |
| | | | 604/9 |
| 2013/0289540 A1 | 10/2013 | Zeltser et al. | |

OTHER PUBLICATIONS

Non-Final Office Action for U.S. Appl. No. 14/182,418, dated Oct. 26, 2015, 21 pages.
Final Office Action for U.S. Appl. No. 14/182,418, dated Mar. 15, 2016, 22 pages.
Non-Final Office Action for U.S. Appl. No. 14/182,418, dated Oct. 26, 2016, 27 pages.
Final Office Action for U.S. Appl. No. 14/182,418, dated Jun. 29, 2017, 34 pages.
Non-Final Office Action for U.S. Appl. No. 14/662,986, dated Sep. 28, 2017, 9 pages.
Non-Final Office action for U.S. Appl. No. 14/182,418, dated May 8, 2018, 32 pages.

\* cited by examiner

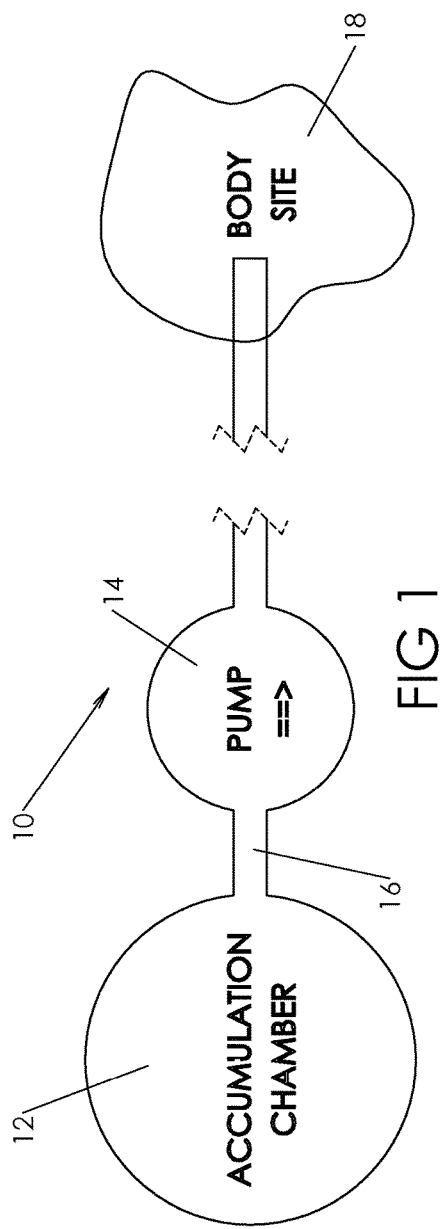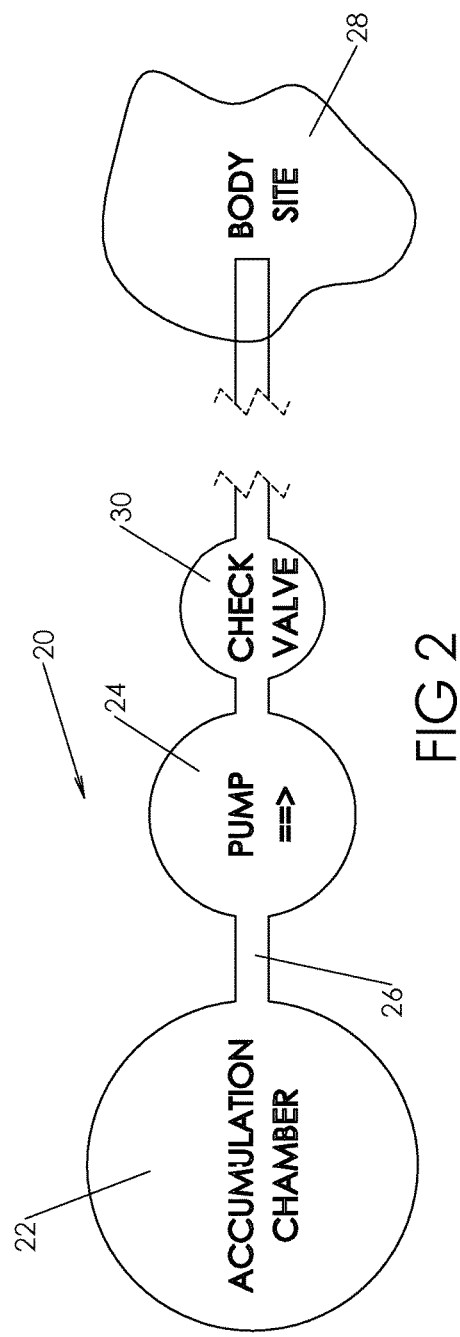

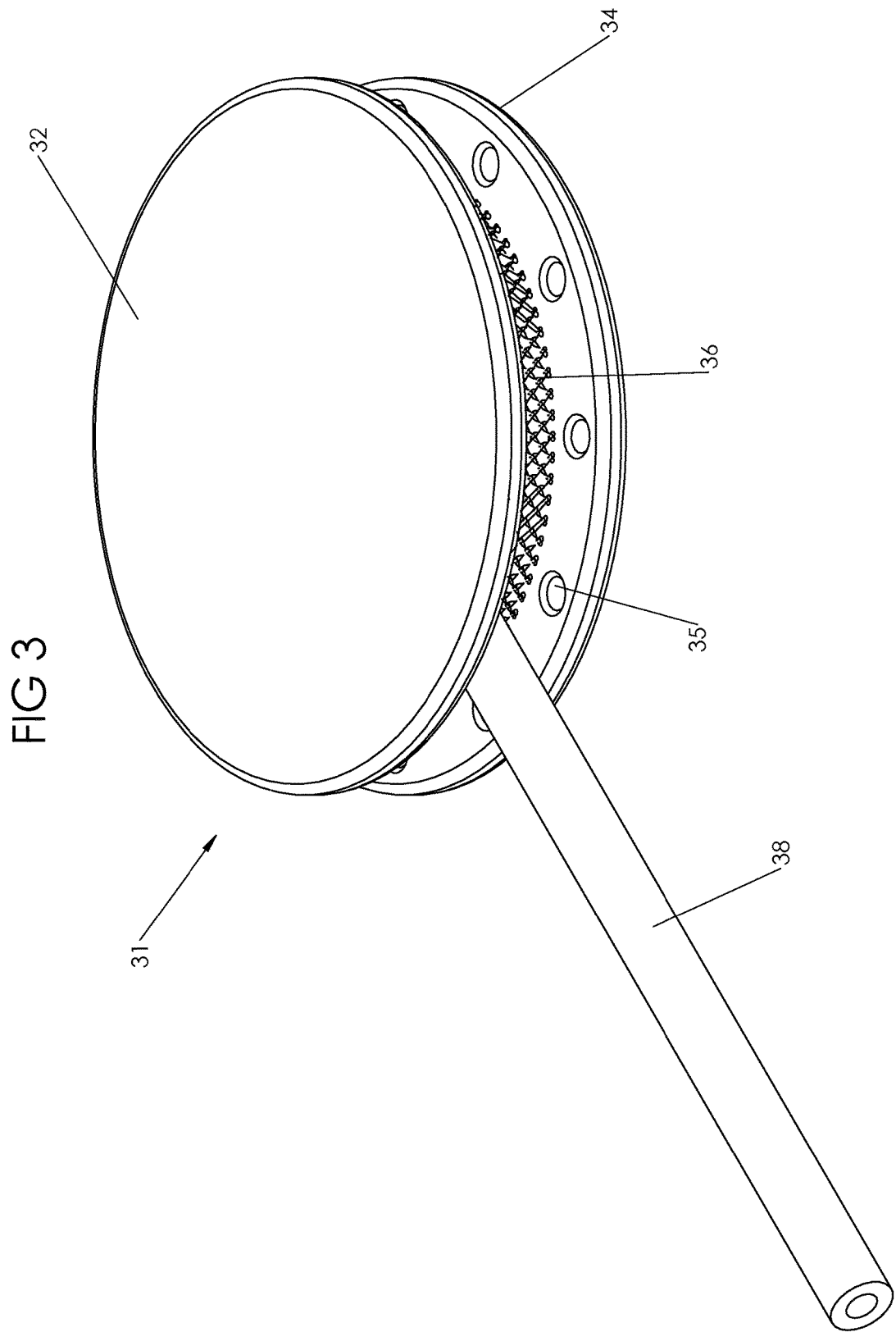

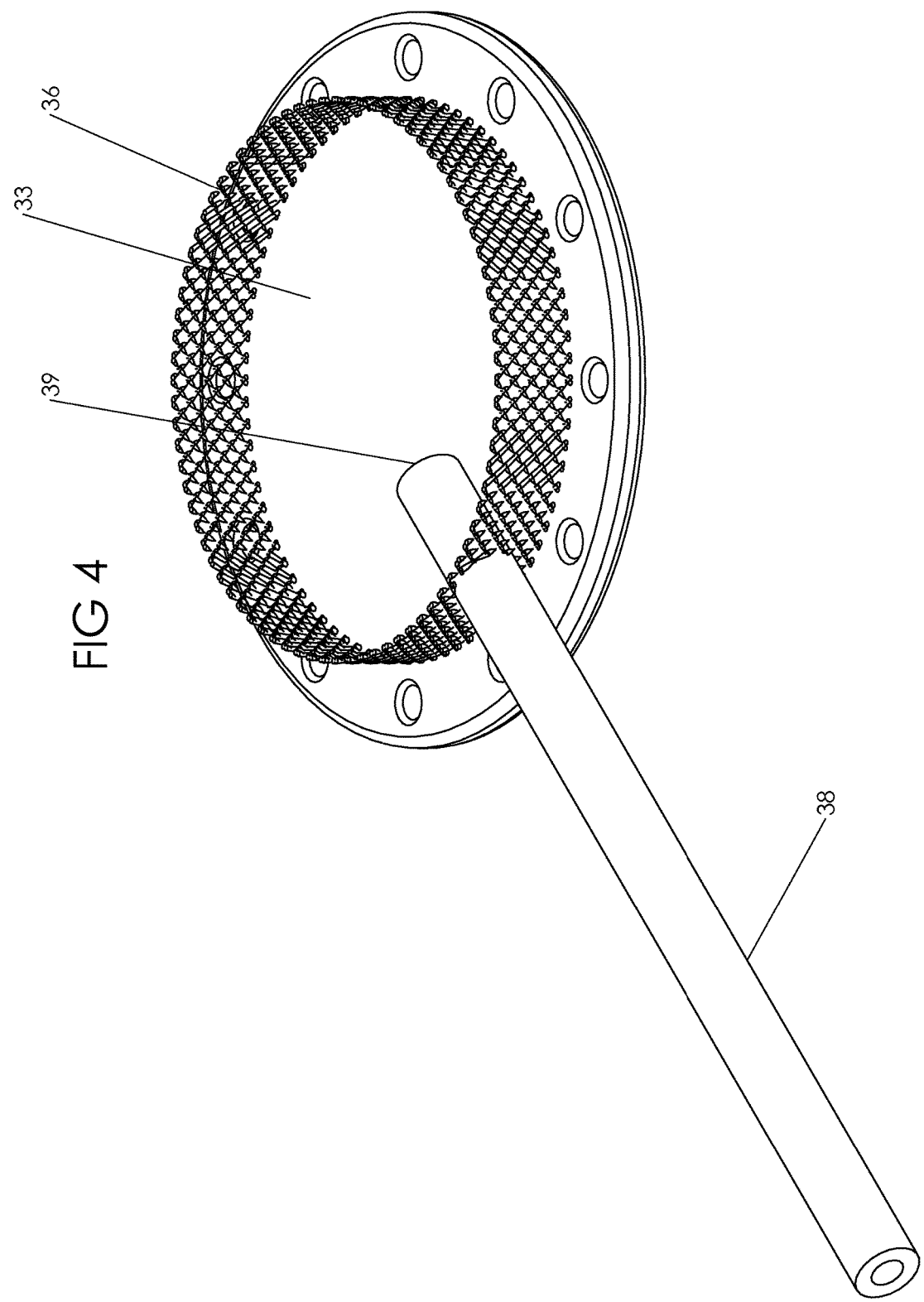

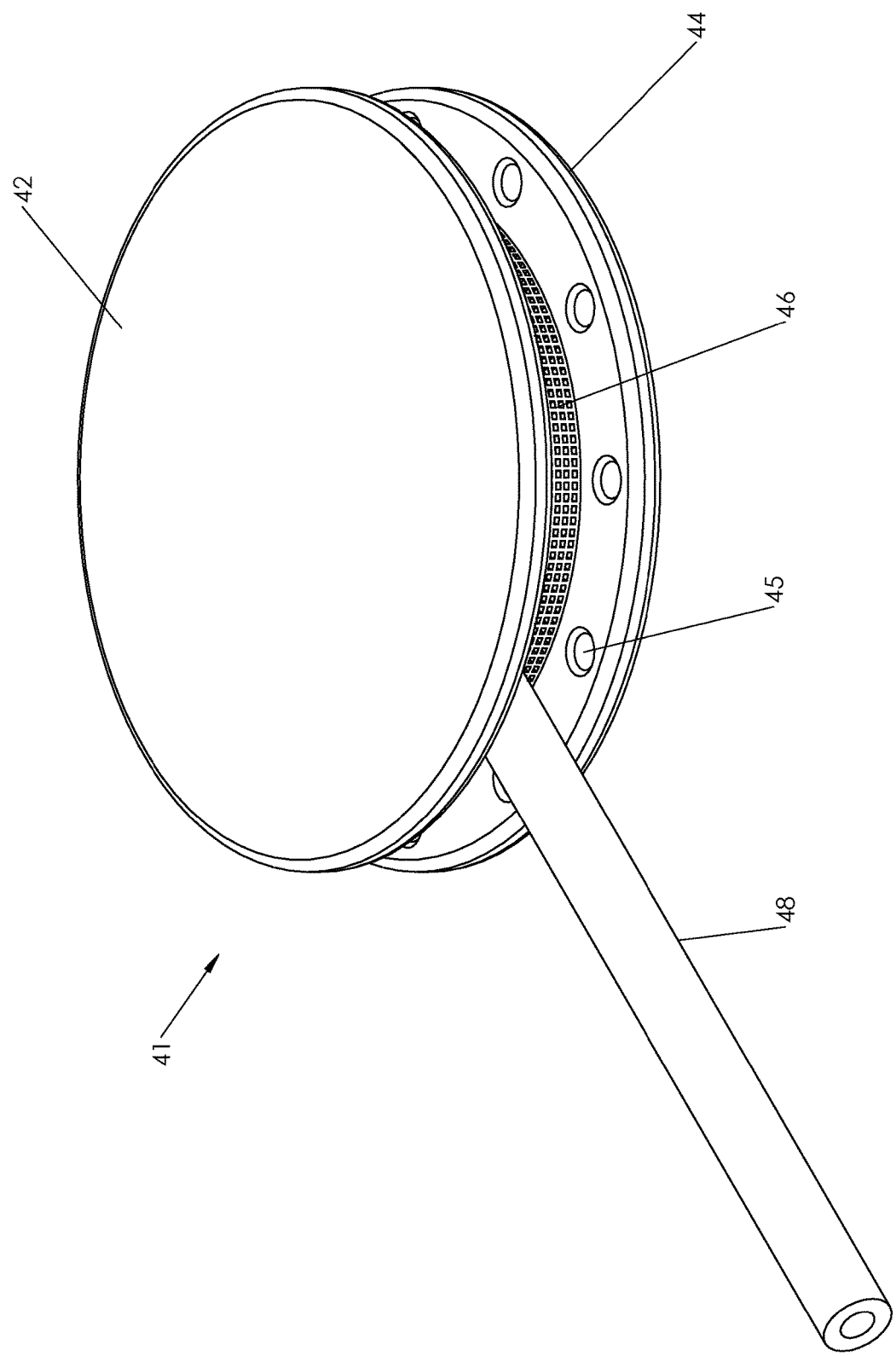

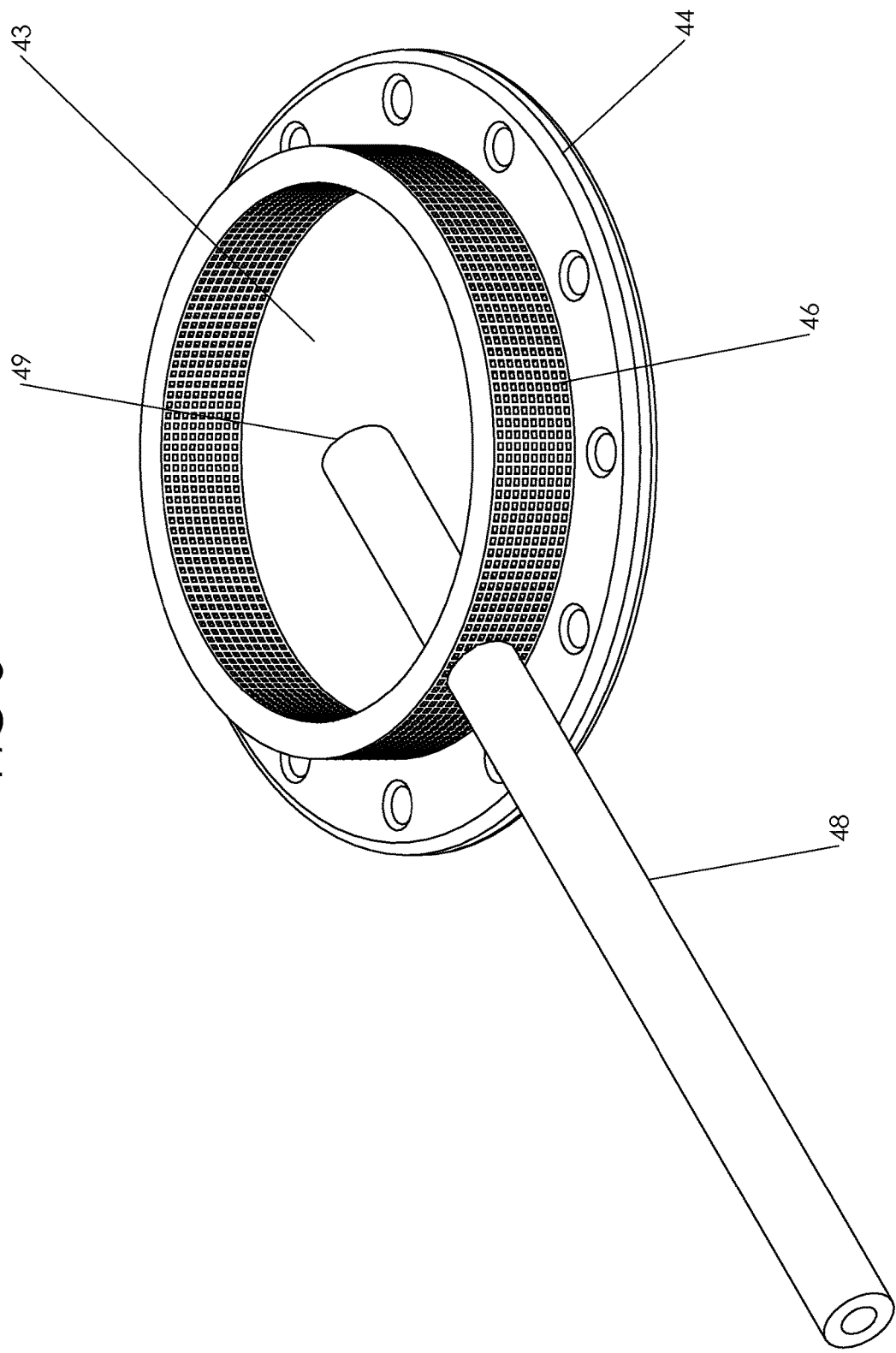

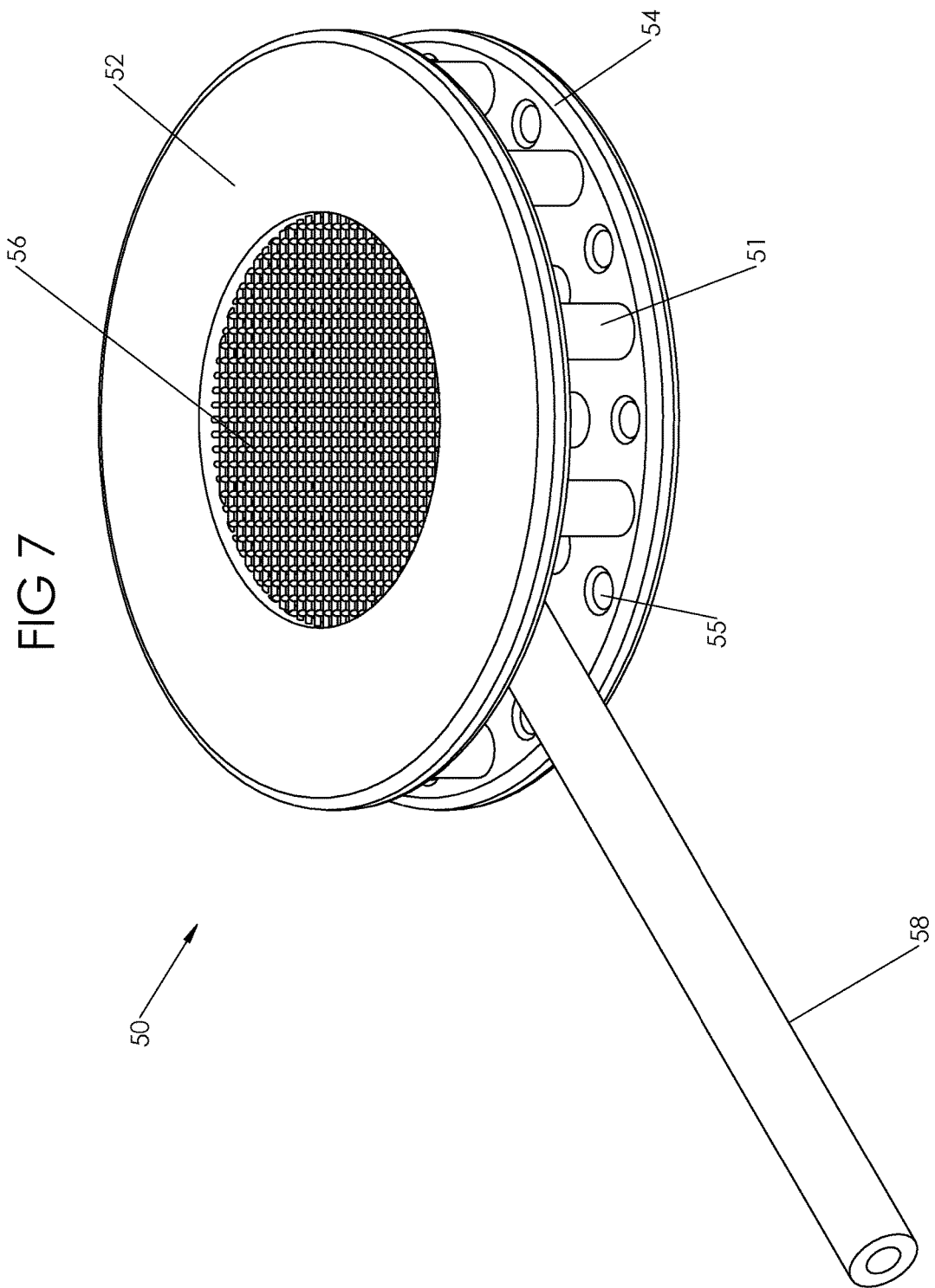

IMPLANTABLE CHAMBER FOR COLLECTION AND SUPPLY OF INTERSTITIAL FLUID

CROSS-REFERENCE TO RELATED APPLICATIONS

This application is a continuation-in-part of U.S. patent application Ser. No. 14/182,418, filed on Feb. 18, 2014, which claims benefit of U.S. Provisional Patent Application No. 61/766,111, filed on Feb. 18, 2013. This application also claims benefit of U.S. Provisional Patent Application No. 62/022,795, filed on Jul. 10, 2014. Said applications are incorporated herein by reference in their entireties.

FIELD OF INVENTION

This application relates to collection and distribution of interstitial fluid for use in medical or veterinary therapy and research.

BACKGROUND OF THE INVENTION

Interstitial fluid is found in the interstitial spaces of a multicellular animal. It is the main component of extracellular fluid and a source of nutrients for the cells. Interstitial fluid contains glucose, salt, fatty acids, minerals such as calcium, magnesium and potassium, as well as oxygen and other components essential to the survival of cells. Interstitial fluid receives its components via capillaries by means of diffusion.

While significant research effort has been expended regarding the use of interstitial fluid as a biomarker for cancer research and diagnosis, research pertaining to use of interstitial fluid for treatment of disease or damaged tissue appears to be lacking. It has now been found that autologous interstitial fluid can be effectively collected in an implanted accumulation chamber and utilized to provide essential sustenance to preselected target cells at a body site remote from the collection site.

It is well known that fibrous tissue tends to encapsulate implanted devices. This fibrous tissue encapsulation of a foreign body is an attempt to extrude it ("marsupialization"), and occurs primarily with non-porous materials. The body attempts to do the same thing with porous materials, but because the surface area is so large, tissue "in-growth", rather than extrusion, occurs. Not only does the pore size of the implant material have an influence, but it is also dependent upon the implant location. With pore sizes ranging from 50-250 microns, only fibrous tissue ingrowth is observed; pore sizes smaller than 50 microns are seen as "non-porous" by the body, while pore sizes of greater than 250 microns result in both fibrous tissue and bony ingrowth. There is a limit, however, as to how far into an implanted device tissue will grow. Blood vessels need to be present near the implanted device in order to nourish and stabilize the ingrowing cells. The accepted distance a cell can live away from a capillary is approximately 50 microns.

The present invention provides an efficient sump for collection of interstitial fluid and includes an accumulation chamber which receives the interstitial fluid from surrounding tissue while minimizing undesirable tissue invasion into the accumulation chamber.

SUMMARY OF INVENTION

Autologous interstitial fluid is collected at a collection site within the patient utilizing a biocompatible sump that provides a fluid accumulation chamber. The accumulated interstitial fluid can then be withdrawn and supplied to a remote body site. A pool of interstitial fluid is accumulated at a first body site within a mammal and at least a portion thereof can then be recovered or dispensed at a second body site remote from the first body site.

The accumulated interstitial fluid can be withdrawn via any number of mechanisms including attaching a catheter to the accumulation chamber, connecting to a puncturable septum containing device, or delivering to or connection to an electromechanical pumping mechanism to deliver the accumulated fluid to any body site.

An implantable, biocompatible system for collecting, distributing or supplying interstitial fluid from the collection site to a remote body site of the patient comprises an accumulation chamber, a confined flow passageway in liquid flow communication with the accumulation chamber, and a liquid transfer pump operably associated with the accumulation chamber to dispense interstitial fluid therefrom to the remote body site through the confined flow passageway.

In one embodiment, the accumulation chamber is a hollow housing provided with at least one biocompatible, liquid permeable interstitial fluid filter such as a screen, mesh, fabric, and the like. A confined flow passageway defined by a catheter and the like is in fluid communication with interior of the housing and serves to withdraw from the chamber collected interstitial fluid.

In one embodiment, the exterior surface of the housing be comprised of the liquid permeable interstitial fluid filter. In another embodiment, a portion of the exterior surface of the housing may be comprised of the liquid permeable interstitial fluid filter.

In another embodiment, the accumulation chamber is comprised of at least two plates or disks wherein a first plate is positioned a given distance from the second plate wherein the center between the first and second plate is open but around the edges or periphery and throughout the internal space of the space between the first and second plate is a plurality of posts or obstructive members between the first and second plate holding the plates apart and creating a tortuous path preventing tissue from growing into the center between the first and second plates. The at least two plates may be flexible, semi rigid or rigid.

In this embodiment, the present invention provides for the accumulation of fluid between and around the posts or obstructive members. The at least two plates may be of any biocompatible material, silicone rubber, polyurethane or biocompatible metal such as stainless steel or titanium. In one embodiment, the surface of the at least two plates may be coated with a material rendering them more biocompatible. Well known in the medical field are Dacron fiber coatings and Parlene style coatings. Any such coating is within the scope of this invention.

In one embodiment, the obstructive members may connect both the first and second plate. In another embodiment, the obstructive members may be of any convention shape including but not limited to spherical, elliptical, tubular, cubical, conical, triangular, rectilinear, polygonal, or any irregular shape having multiple angles or curves. Alternatively, the obstructive members may be web-like or open cellular sponge-like structures.

The accumulation chamber may be any conventional shape and thickness depending on the required fluid to be collected and the location/placement of the present invention in the body or use including but not limited to spherical, elliptical, tubular, cubical, or rectilinear. Alternatively, the accumulation chamber may be an irregular shape such as a flattened disk. The accumulation chamber has an open interior area and may have one or more outlets for the interstitial fluid. The size and shape of the accumulation chamber depends on the location where it is to be implanted and on the amount of interstitial fluid to be collected. The chamber is designed to prevent occlusion by ingrowing tissue. This is accomplished by creating a tortuous pathway into the accumulation chamber. This can be accomplished in a number of ways. In one embodiment, the accumulation chamber is disk shaped wherein the accumulation chamber is comprised of a solid top plate and solid bottom plate having a peripheral filter that extends the top plate to the bottom plate. The filter may be fabricated from densely compacted filter material where the pore size of the pathway is in the range of about 1 micron to about 100 microns, preferably about 20 microns to about 30 microns. The filter can be a screen or a mesh, or fabricated from a sintered metal filter material where the pore size is selected to protect the interior from tissue invasion.

In one embodiment, the accumulation chamber may have at least one septum in the exterior surface of the accumulation chamber thereby allowing a user to access the interior of the accumulation chamber and withdraw accumulated fluid. In another embodiment, the accumulation chamber be further comprised of at least one flexible dome wherein such at least one flexible dome may include a material that allows for the accumulation of fluid within such dome that may be accessible by a user.

BRIEF DESCRIPTION OF DRAWINGS

In the drawings,

FIG. 1 is a schematic representation of an interstitial fluid delivery system comprising an interstitial fluid collection chamber in communication with a confined flow passageway and having a liquid transfer pump in the confined flow passageway;

FIG. 2 is a schematic representation of an interstitial fluid delivery system comprising an interstitial fluid collection chamber in communication with a confined flow passageway and having a unidirectional check-valve in the confined flow passageway;

FIG. 3 is an isometric view of an embodiment of the present invention showing a hollow accumulation chamber defined by spaced plates and in part by a peripheral liquid permeable filter;

FIG. 4 is an isometric view of the embodiment snow in FIG. 4 with the top plate removed to show the details of the interior of the accumulation chamber;

FIG. 5 is an isometric view of an embodiment of the present invention showing a hollow accumulation chamber defined by spaced plates and in part by a circular liquid permeable filter;

FIG. 6 is an isometric view of the embodiment shown in FIG. 5 with top plate removed to show details of the interior of the accumulation chamber;

FIG. 7 is an isometric view of an embodiment of the present invention showing a hollow accumulation chamber defined by spaced plates and provided with a liquid permeable filter framed in a plate defining in part the chamber;

DESCRIPTION OF PREFERRED EMBODIMENTS

Figure 8:
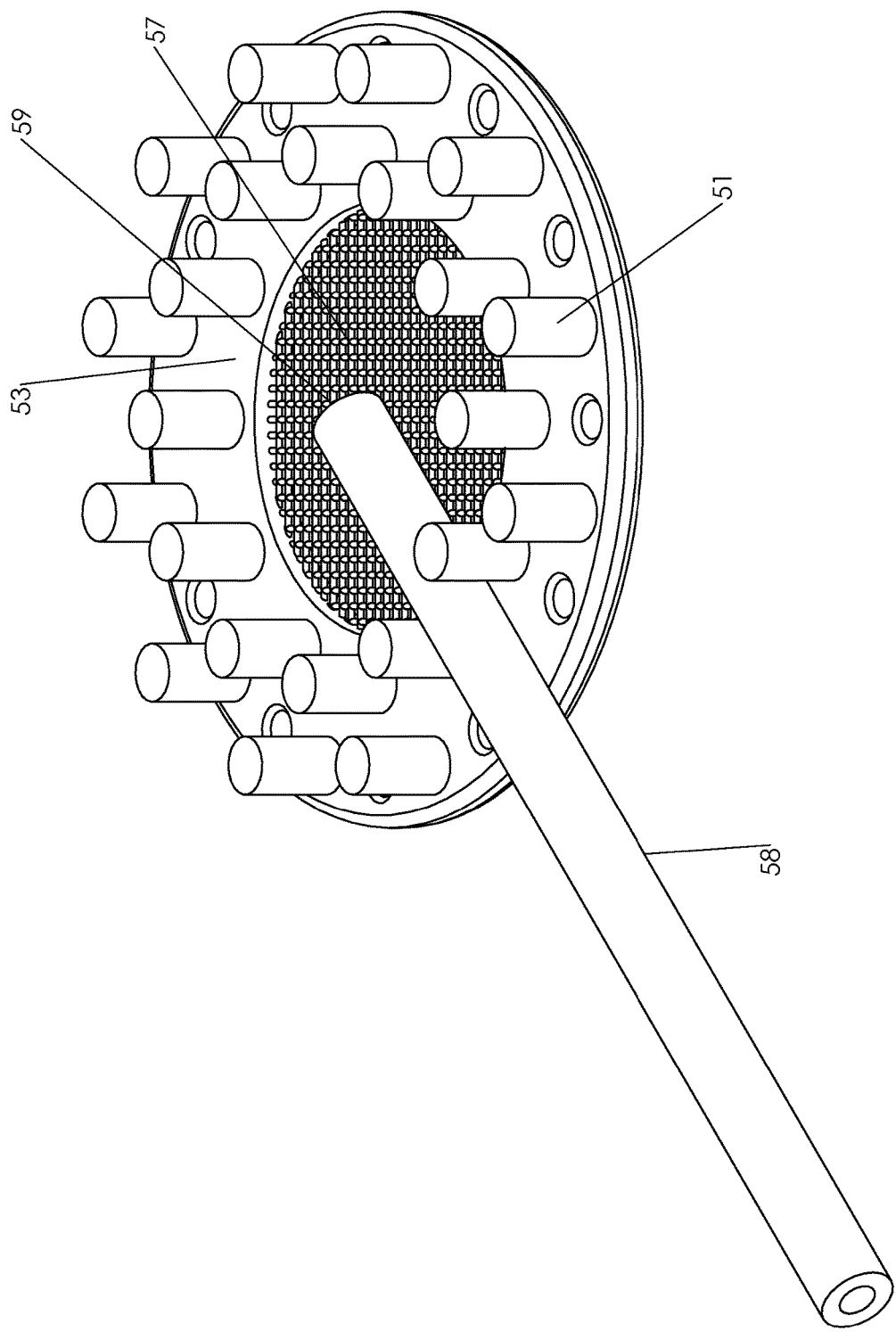
FIG. 8 is an isometric view of the embodiment shown in FIG. 7 with top plate removed to show details of the interior of the accumulation chamber.

Referring to the drawings, FIG. 1 schematically illustrates an implantable, biocompatible sump that utilizes an accumulation chamber embodying the invention. Sump 10 comprises an implantable accumulation chamber 12, liquid transfer pump 14, and a confined flow passageway such as outlet catheter 16 which is in liquid flow communication with accumulation chamber 12. Outlet catheter 16 dispenses interstitial fluid collected in accumulation chamber 12 at a preselected body site 18 which is populated by cells in need of additional nutrients. Body site 18 can be a lesion such as damaged tissue, an open wound, and the like, or transplanted cells such as the Islets of Langerhans for treatment of diabetes, autologous and allogeneic pluripotent stem cells, and the like.

Transport of interstitial fluid from accumulation chamber 12 to body site 18 is facilitated by liquid transfer pump 14. Various types of pumps can be utilized for this purpose, such as a peristaltic pump, a gear pump, a piston-type metering pump, an elastomeric dome integral with a housing portion of accumulation chamber 12 and in communication with outflow catheter 16. In certain applications a programmable, computer controlled electromechanical pump may be used, as in the case of insulin delivery where various flow rates are required during a normal day. Feedback from a sensor either integral with the pump or situated in a predetermined remote location may be used to regulate the pumping rate, which may be continuous or intermittent.

FIG. 2 shows an alternate embodiment of a sump embodying the invention. In particular, sump 20 comprises accumulation chamber 22, liquid transfer pump 24, catheter 26 in liquid flow communication with accumulation chamber 22, and unidirectional flow check valve 30 downstream from liquid transfer pump 24 and associated with the confined flow passageway defined by catheter 26.

The relative locations of liquid transfer pump 24 and check-valve 30 can be interchanged, if desired, for a particular application. In some instances the check-valve can be situated at an exit port of accumulation chamber 22.

FIGS. 3 and 4 show a housing which provides a hollow accumulation chamber 31 defined by first plate 32, second plate 34 and liquid permeable circumferential filter 36 which maintains first plate 32 and second plate 34 in a spaced relationship to one another. The spacing between plates is predetermined to minimize tissue from growing over the plates and occluding the plates. The plates can be fabricated of medical grade materials such as pliable medical grade rubber, e.g., certified USP Class V or Class VI materials, or any other biocompatible elastomeric material, of stainless steel, of titanium, and the like biocompatible material of construction.

Filter 36 is affixed to plate 32 and plate 34, and maintains these plates in a spaced relationship relative to one another. Liquid permeable interstitial fluid filter 36 also is made of a biocompatible material and can be a screen, such as a metal screen, made from stainless steel, or titanium, and the like, a mesh, such as plastic mesh, made from a polyolefin material such as polypropylene, polyethylene, and the like, or a stiff woven fabric such as polyethylene terephthalate (Dacron), and the like. In the case of a woven fabric filter, spacer posts can be utilized as well to maintain the desired spacing if necessary.

The spacing between the plates is selected so that surrounding tissue does not grow across the gap defined by first plate 32 and second plate 34. The spacing preferably is in the range of about 1.5 millimeters (mm) to about 5 mm, more preferably about 3 mm.

Center portion 33 (FIG. 4) of accumulation chamber 31 is open and allows for interstitial fluid accumulation.

Access to center portion 33 is provided by catheter 38 which extends into center portion 33 and defines access aperture 39 at the proximal end portion of catheter 38.

Plural peripheral apertures, such as aperture 35 in internal plate 34, are provided for securing hollow accumulation chamber 31 to adjacent tissue with sutures and the like.

A typical accumulation chamber, usually having a round configuration, has an external diameter of about 45 to 50 mm, and a plate thickness of about 1.5 mm for the first plate and the second plate. The plate spacing is about 3 to about 3.25 mm. Other accumulation chamber overall configurations such as square, polygonal, polyhedron, elliptical, spherical, kidney-shaped, and the like, can be utilized, depending on the implant site.

FIGS. 5 and 6 show accumulation chamber 41 similar to that shown in FIGS. 3 and 4, except that circumferential or circular filter 46 between spaced plates 42 and 44 is a polyolefin mesh, i.e., a polyethylene or polypropylene mesh, permeable to interstitial fluid.

Catheter 48 provides access to interior portion of chamber 41 and has access aperture 49 and the proximal end thereof.

Plural spaced peripheral apertures, such as peripheral aperture 45 in internal 45, are provided for securing accumulation chamber 41 to adjacent tissue with sutures and the like.

The embodiment illustrated in FIGS. 7 and 8 provides an interstitial fluid filter portion framed in at least one of the first and second plates while maintaining the desired spacing between the plates using a plurality of spacer posts. The filter portion can be a screen, a mesh, a fabric, and the like. In particular, interstitial fluid accumulation chamber 50 has a first plate 52 and second plate 54 held in a spaced relationship relative to one another using plural spacer posts such as spacer post 51 integral with first plate 52 as well as with second plate 54. Interstitial fluid filters 56 and 57 are framed in first plate 52 and second plate 54, respectively. If desired, first plate filter 56 on second plate filter 58 can be replaced by a septum for access to accumulation chamber interior 53.

Catheter 58 provides access to chamber interior 53 via aperture 59, and plural spaced apertures, such as aperture 55 in second plate 54 facilitate securement of accumulation chamber 50 to surrounding tissue.

Figure 9:
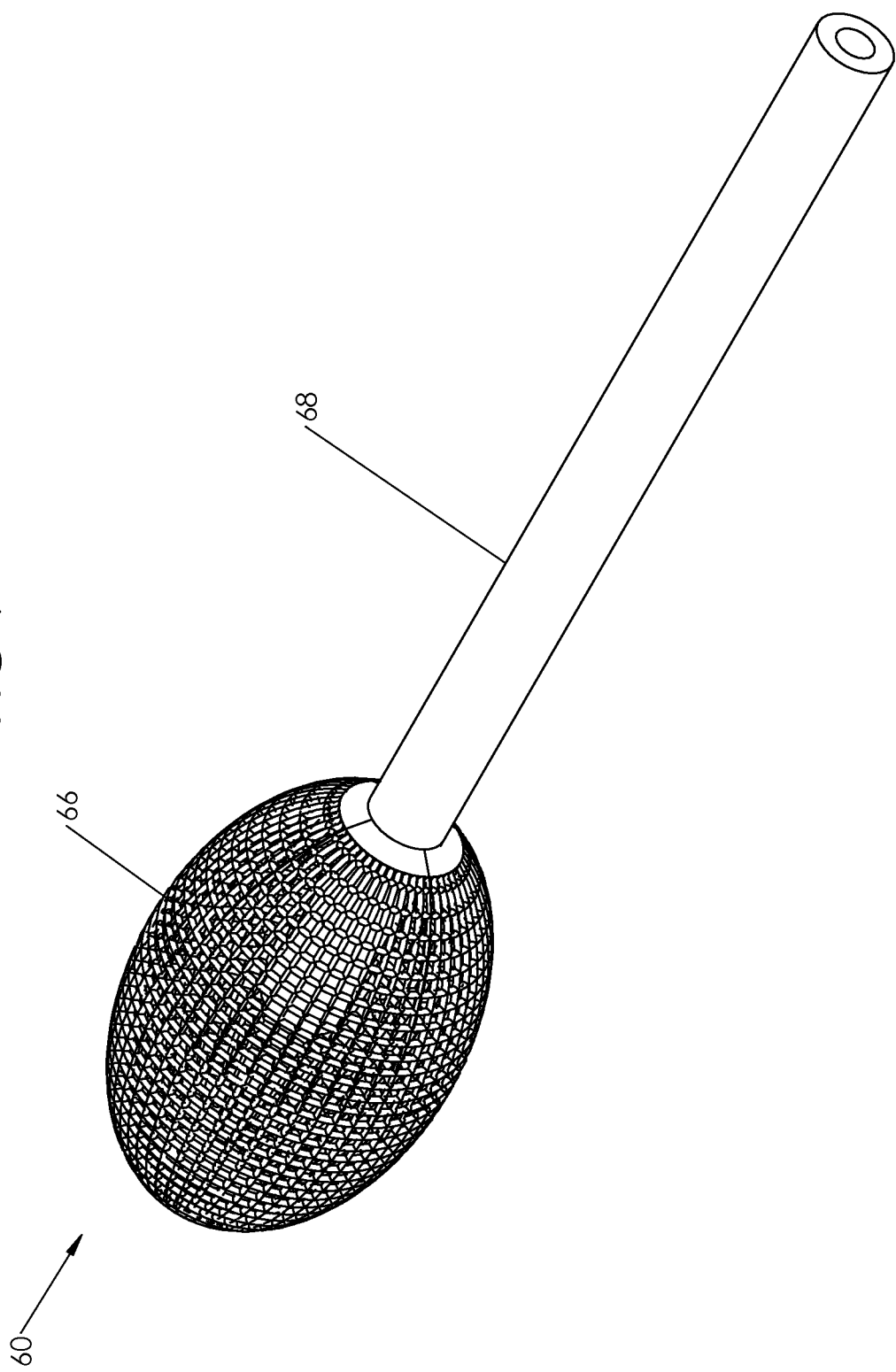
FIG. 9 is an isometric view of an embodiment of the present invention showing a hollow accumulation chamber in the shape of an ellipsoid.

FIG. 9 illustrates an implantable interstitial fluid accumulation chamber having the shape of an oblate ellipsoid. In particular hollow interstitial accumulation chamber 60 is defined by a biocompatible, liquid permeable filter 66 which substantially extends over the entire outer surface of the ellipsoid and can be a metal screen, plastic mesh, liquid permeable woven fabric stretched over a frame, and the like. Catheter 68 enters hollow accumulation chamber 60 along the major axis of the oblate ellipsoid.

Figure 10:
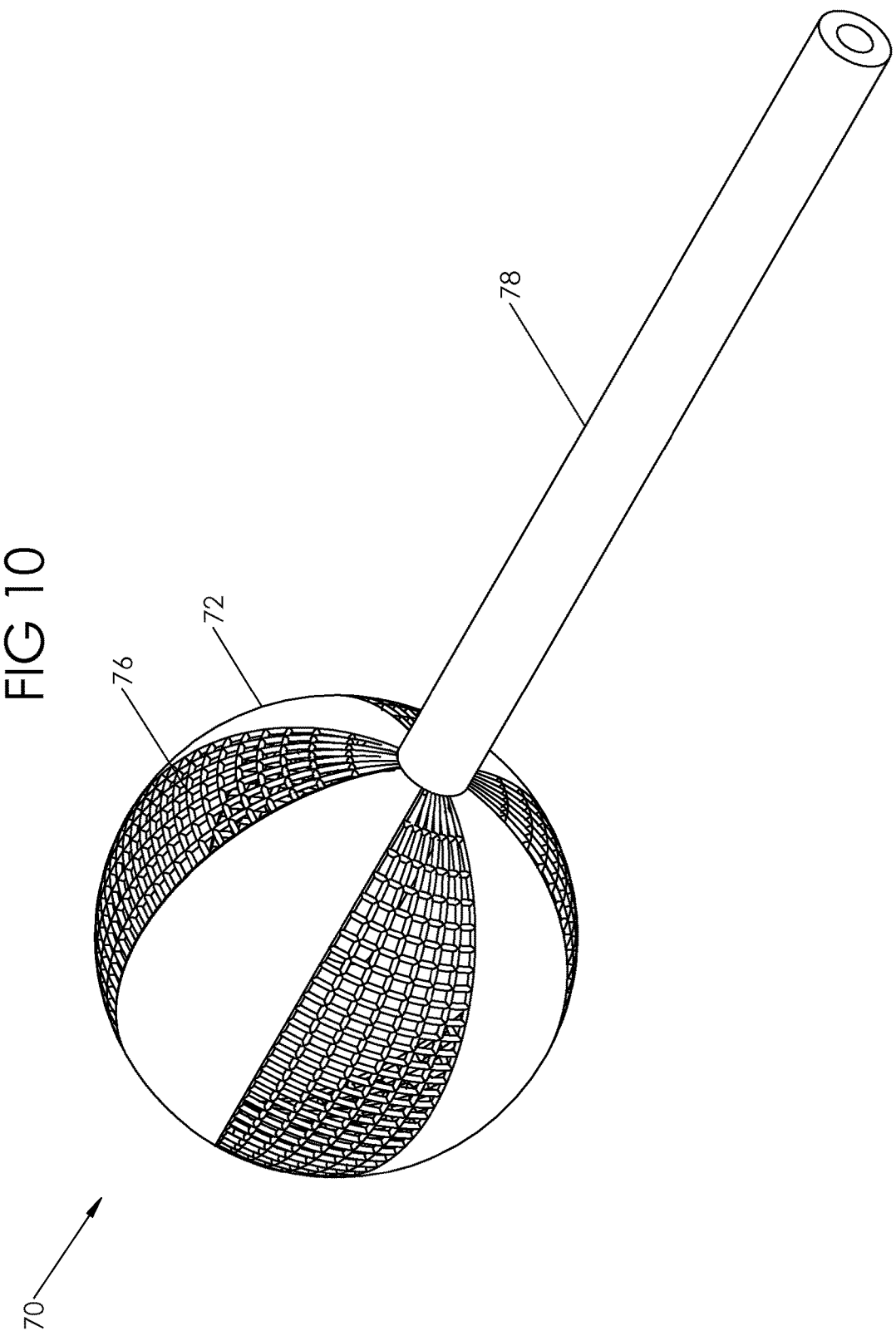
FIG. 10 is an isometric view of an embodiment of the present invention showing a hollow accumulation chamber in the shape of a sphere defined in part by liquid permeable panels.

FIG. 10 illustrates an implantable accumulation chamber having the shape of a hollow spheroid. In particular, accumulation chamber 70 comprises alternating liquid permeable panels 76 and liquid permeable panels 72. Liquid permeable panels 76 each comprise a filter for the interstitial fluid while liquid impermeable panels 72 contribute to the overall structure of the chamber. Catheter 78 integral with chamber 70 is in liquid flow communication with chamber interior and provides access to the chamber interior. If desired, the entire outer surface of the spheroid can be liquid permeable and serve as an interstitial fluid filter.

Figure 11:
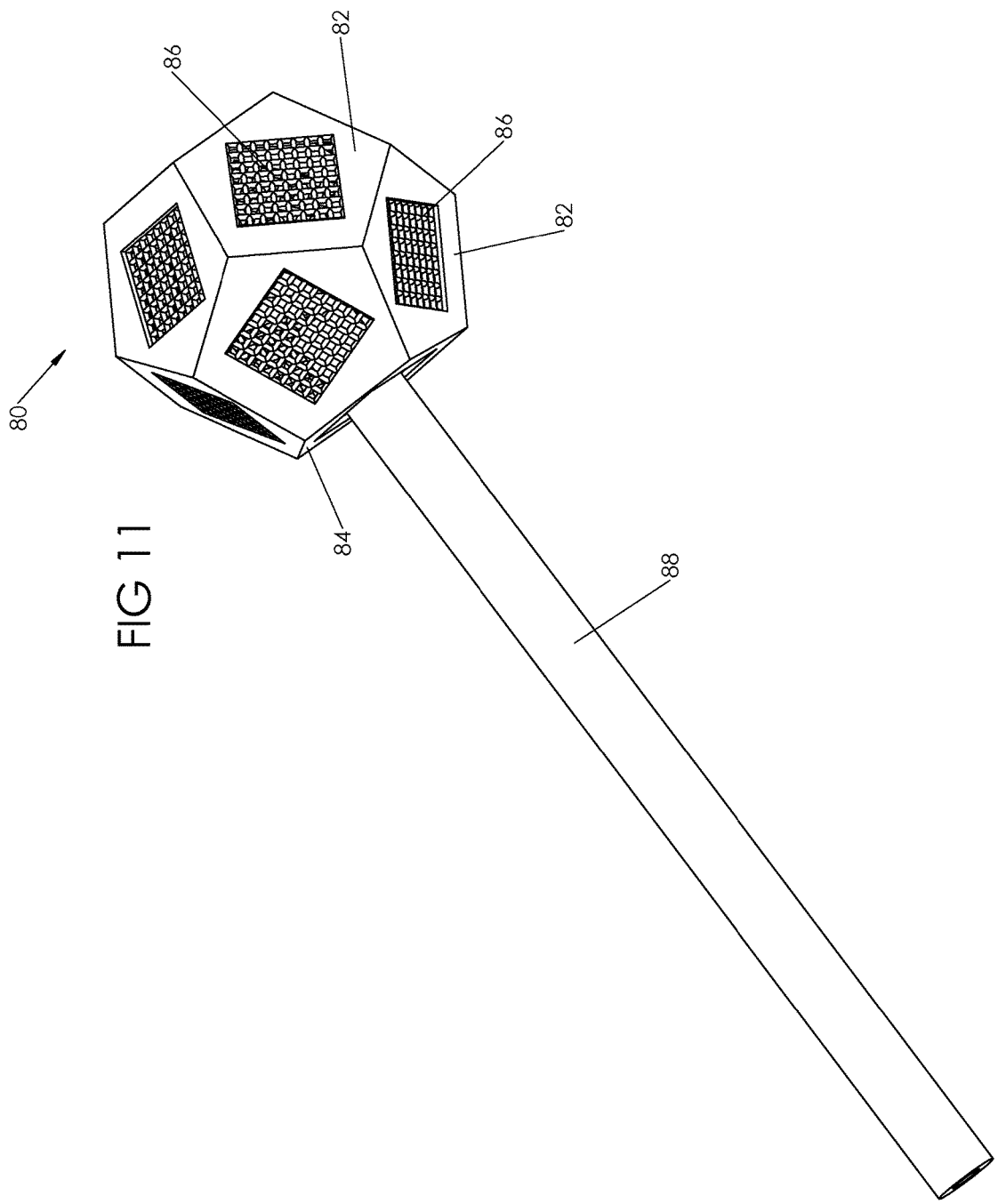
FIG. 11 is an isometric view of an embodiment of the present invention showing a hollow accumulation chamber in the shape of a regular dodecahedron, with each panel of the dodecahedron including a liquid permeable filter.

FIG. 11 illustrates an implantable accumulation chamber having the shape of a polyhedron, specifically, a regular dodecahedron, constituted by twelve substantially flat panels each having the configuration of a regular pentagon. Eleven of the panels frame a liquid permeable, interstitial fluid filter while one panel, the base panel, provides entry port for fluid withdrawal catheter. In particular, accumulation chamber 80 is defined by eleven contiguous filter panels 82 each including filter portion 86, and base panel 84 which is integral with catheter 88. The number of panels provided with the filter can vary; however, at least one of the panels includes an interstitial fluid filter.

The interstitial fluid accumulation chamber described hereinabove are suitable for human as well as veterinary applications that involve collection of interstitial fluid.

The accumulated interstitial fluid can be withdrawn from the chamber or transported to a desired location by an electromechanical or mechanical pump connected to or fixed to the accumulation chamber. A benefit of the present invention is that the interstitial fluid, naturally occurring in the body, can be collected and then conveyed to any location in need of nutrients and oxygen.

The foregoing specification and the drawings are illustrative, and are not intended to be limiting. Still other variations within the spirit and scope of the present invention are possible and will readily present themselves to one skilled in the art.

The invention claimed is:

1. An implantable, biocompatible interstitial fluid sump which comprises:
    an accumulation chamber comprising a first plate, a second plate in juxtaposition relative to the first plate, and an interstitial fluid filter framed in the first plate or the second plate, the interstitial fluid filter being porous, liquid permeable, made from a biocompatible material, and having a pore size in a range of 1 micron to 100 microns to protect the accumulation chamber from tissue invasion; and
    a confined flow passageway in fluid flow communication with the accumulation chamber.

2. The interstitial fluid sump in accordance with claim 1 wherein a plurality of posts join the first and second plates.

3. The interstitial fluid sump in accordance with claim 1 wherein at least one obstructive member is connected to and situated between the first and second plates.

4. The interstitial fluid sump in accordance with claim 1 wherein at least one portion of one of the first and second plates is comprised of a flexible material to provide access to accumulated interstitial fluid.

5. The interstitial fluid sump in accordance with claim 1 wherein at least one of the first and second plates comprises an elastomeric septum to provide access to accumulated interstitial fluid.

6. The interstitial fluid sump in accordance with claim 1 wherein a separate, respective interstitial fluid filter is framed in each of the first and second plates.

7. The interstitial fluid sump in accordance with claim 1 wherein the interstitial fluid filter is a screen.

8. The interstitial fluid sump in accordance with claim 7 wherein the screen comprises a biocompatible polymeric screen, a stainless steel screen, or a titanium screen.

9. The interstitial fluid sump in accordance with claim 1 wherein the interstitial fluid filter is a mesh.

10. The interstitial fluid sump in accordance with claim 9 wherein the mesh is a polyolefin, polypropylene, or polyolefin mesh.

11. The interstitial fluid sump in accordance with claim 1 wherein the interstitial fluid filter is a woven fabric.

12. The interstitial fluid sump in accordance with claim 11 wherein the woven fabric is polyethylene terephthalate.

13. The interstitial fluid sump in accordance with claim 1 wherein the accumulation chamber includes a septum for withdrawal of accumulated interstitial fluid.

14. The interstitial fluid sump in accordance with claim 1 wherein the interstitial fluid filter has a pore size in a range of 20 microns to 30 microns to protect the accumulation chamber from tissue invasion.

15. The interstitial fluid sump in accordance with claim 1 wherein the first and second plates are spaced apart at a distance which minimizes tissue from growing over and occluding them.

16. The interstitial fluid sump in accordance with claim 15 wherein the distance is in a range of 1.5 millimeters to 5 millimeters.

17. The interstitial fluid sump in accordance with claim 1 wherein the accumulation chamber comprises a plurality of posts forming a tortuous path which prevents tissue from growing within the accumulation chamber.

* * * * *